US011369495B2

(12) United States Patent
Koppe

(10) Patent No.: US 11,369,495 B2
(45) Date of Patent: Jun. 28, 2022

(54) PROSTHESIS SYSTEM WITH A LINER AND A PROSTHESIS SOCKET

(71) Applicant: Ottobock SE & Co. KGaA, Duderstadt (DE)

(72) Inventor: Mario Koppe, Göttingen (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 0 days.

(21) Appl. No.: 15/733,062

(22) PCT Filed: Nov. 5, 2018

(86) PCT No.: PCT/EP2018/080102
§ 371 (c)(1),
(2) Date: May 5, 2020

(87) PCT Pub. No.: WO2019/091891
PCT Pub. Date: May 16, 2019

(65) Prior Publication Data

US 2020/0289296 A1 Sep. 17, 2020

(30) Foreign Application Priority Data

Nov. 10, 2017 (DE) ..................... 10 2017 126 462.0

(51) Int. Cl.

| | |
|---|---|
| ***A61F 2/78*** | (2006.01) |
| ***A61F 2/80*** | (2006.01) |
| ***A61F 2/72*** | (2006.01) |
| ***A61F 2/70*** | (2006.01) |

(52) U.S. Cl.
CPC .............. *A61F 2/70* (2013.01); *A61F 2/7812* (2013.01); *A61F 2/80* (2013.01); *A61F 2/72* (2013.01)

(58) Field of Classification Search
CPC ...... A61F 2/72; A61F 2/60; A61F 2/80; A61F 2/7212; A61F 2002/607; A61F 2/7812
See application file for complete search history.

(56) References Cited

U.S. PATENT DOCUMENTS

| | | | | |
|---|---|---|---|---|
| 5,258,037 | A | 11/1993 | Caspers | |
| 5,443,525 | A * | 8/1995 | Laghi | A61F 2/72 600/384 |
| 8,591,599 | B1 | 11/2013 | Kaliki et al. | |
| 9,155,634 | B2 | 10/2015 | Lipschutz et al. | |
| 9,744,056 | B2 | 8/2017 | Kuiken et al. | |

(Continued)

FOREIGN PATENT DOCUMENTS

| | | | |
|---|---|---|---|
| DE | 202010005472 | U1 | 9/2010 |
| DE | 102014106070 | A1 | 11/2015 |

(Continued)

*Primary Examiner* — Bruce E Snow
(74) *Attorney, Agent, or Firm* — Holland & Hart LLP

(57) ABSTRACT

A prosthesis system with a liner and a prosthesis socket, wherein the liner includes a closed distal end, an open proximal end, a lateral surface, which extends from the distal end to the proximal end, and a first connection device. The prosthesis socket includes a second connection device, which is configured to interact with the first connection device. The first connection device is arranged on the lateral surface, and the first connection device and the second connection device are configured to establish a mechanical locking and an electrical contact between the liner and the prosthesis socket.

17 Claims, 6 Drawing Sheets

(56) References Cited

U.S. PATENT DOCUMENTS

| | | | | |
|---|---|---|---|---|
| 2007/0021841 | A1 | 1/2007 | Al-Temen et al. | |
| 2009/0132056 | A1 | 5/2009 | Kania | |
| 2009/0216339 | A1* | 8/2009 | Hanson | A61B 5/296 623/25 |
| 2012/0296445 | A1* | 11/2012 | Leiniger | A61F 2/7812 623/25 |
| 2013/0046394 | A1 | 2/2013 | Lipschutz et al. | |
| 2014/0018938 | A1* | 1/2014 | Bertels | A61F 2/7812 623/25 |
| 2016/0038314 | A1* | 2/2016 | Kuiken | A61F 2/76 623/36 |

FOREIGN PATENT DOCUMENTS

| | | | |
|---|---|---|---|
| GB | 2542636 | A | 3/2017 |
| WO | 2008040286 | A1 | 4/2008 |

* cited by examiner 2
4
6
8
10
12
14
16
18
20
22
24
D1
D2

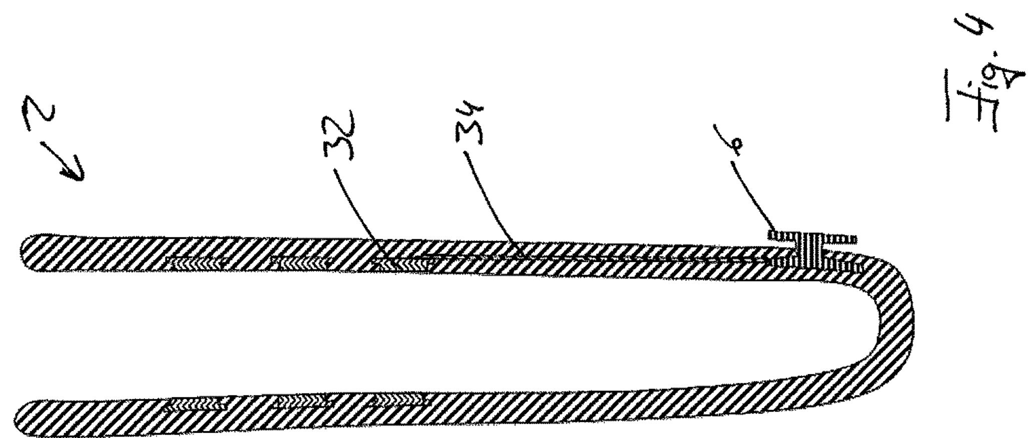
2
32
34
6
Fig. 4
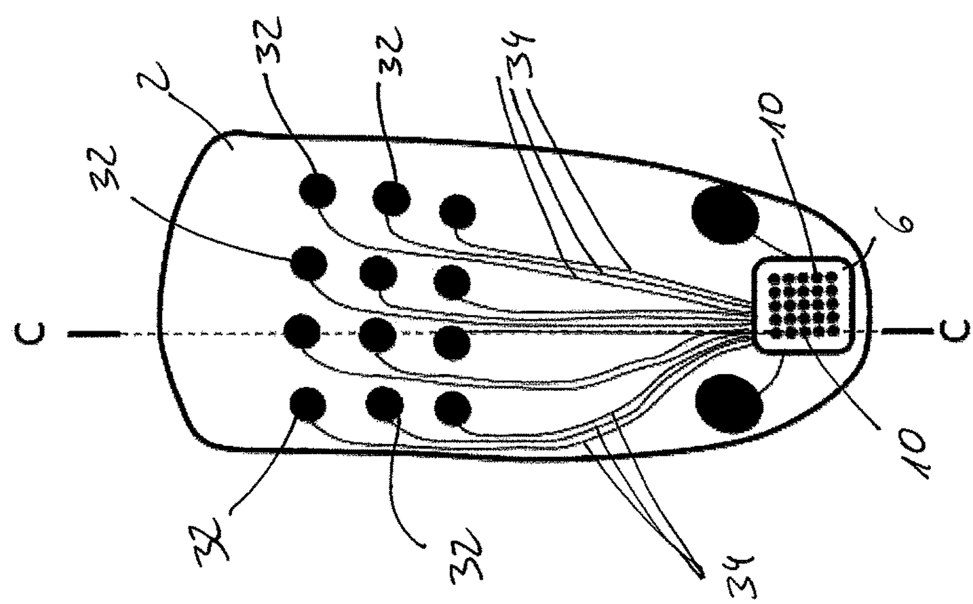
2
32
34
10
6
C
C

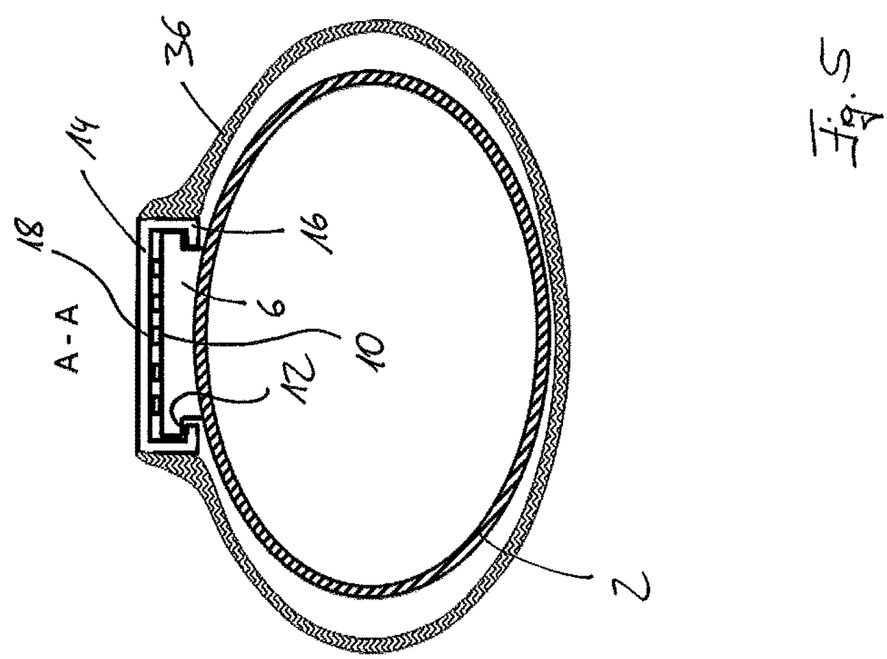
Fig. 5
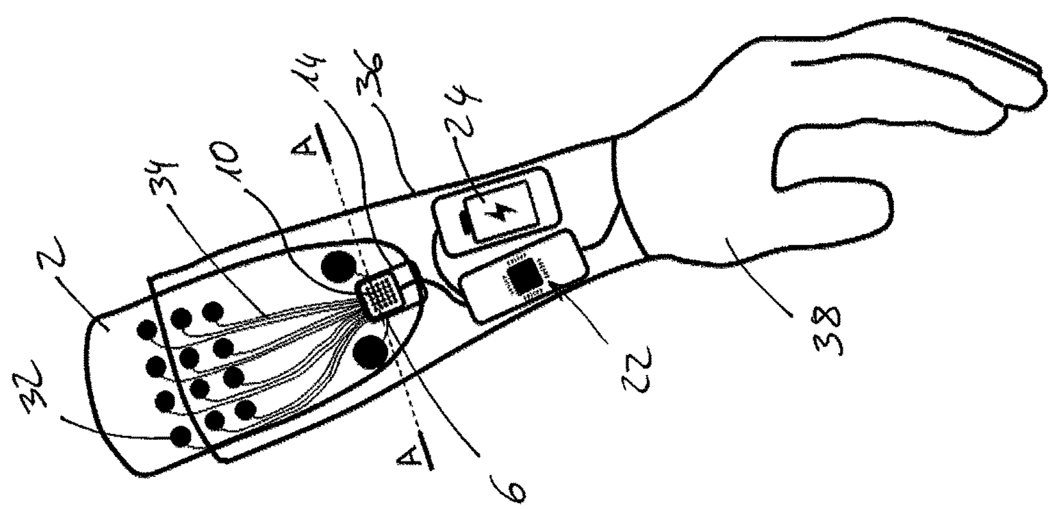

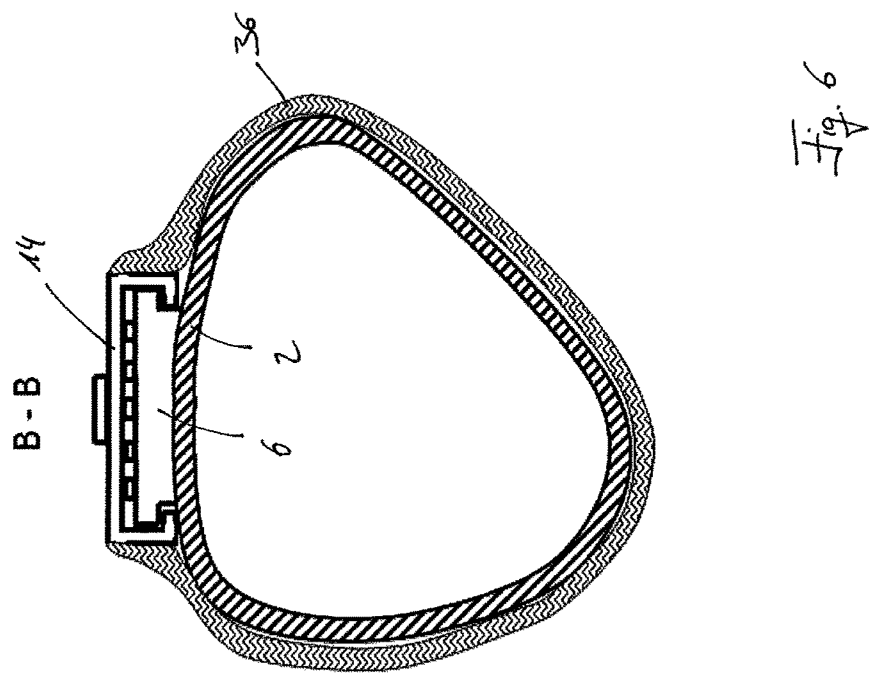
Fig. 6
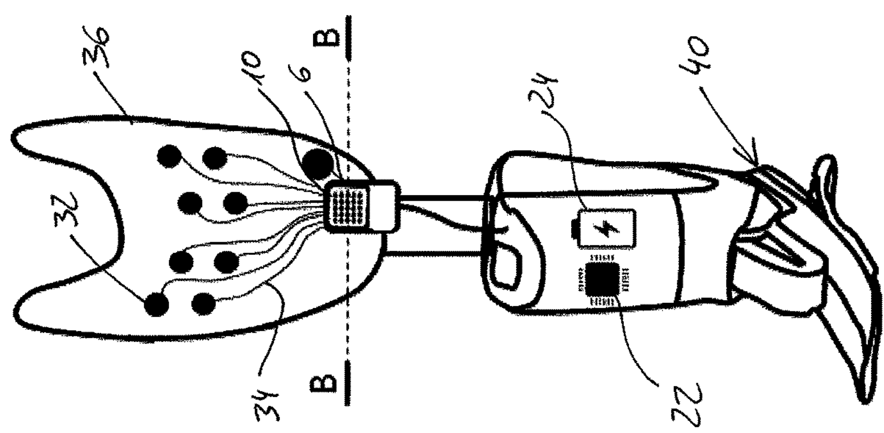

PROSTHESIS SYSTEM WITH A LINER AND A PROSTHESIS SOCKET

CROSS REFERENCE TO RELATED APPLICATIONS

This application is a U.S. National Entry and claims priority to PCT International Patent Application No. PCT/EP2018/080102, filed 5 Nov. 2018 and entitled "PROSTHESIS SYSTEM WITH A LINER AND A PROSTHESIS SOCKET," which claims priority to Germany Patent Application No. 10 2017 126 462.0 filed 10 Nov. 2017, the entire disclosures of which are incorporated herein by this reference.

TECHNICAL FIELD

The invention relates to a prosthesis system with a liner and a prosthesis socket, wherein the liner comprises a closed distal end, an open proximal end, a lateral surface that extends from the distal end to the proximal end, and a first connection device, and wherein the prosthesis socket has a second connection device which is configured to interact with the first connection device.

BACKGROUND

A wide range of configurations of such prosthesis systems are known from the prior art. In order to use the prosthesis system, the liner is first pulled over the amputation stump, primarily by rolling it up. The amputation stump is then inserted into the prosthesis socket with the overlying liner and subsequently fixed to it. This may be achieved using negative pressure by suctioning the space between the liner and the prosthesis socket. If this type of attachment is not sufficient or wanted, there are many different connection devices available that can connect the liner to the prosthesis socket. For example, U.S. Pat. No. 9,744,056 B2 describes such connection devices. At its distal end, the liner features a pin that is inserted into a specially provided opening in the prosthesis socket and locked there. This may result in snap connections or, for instance, magnetic connections between the connection devices. A prosthesis system is known from U.S. Pat. No. 9,155,634 B2 with which the liner is fixed in the prosthesis socket by connecting the first connection device, which is arranged at the distal end of the liner, to the corresponding second connection device of the prosthesis socket.

In many cases, modern liners now feature electrodes which are poured or stuck in an electrically non-conductive liner base material. These electrodes may form a flush surface with or protrude from the inner side of the liner, which faces away from the amputation stump. When the liner is mounted, they come into contact with the skin of the wearer of the prosthesis system and can thus pick up electrical signals from the skin of the wearer or transmit them, for example to underlying muscles. If electrical signals are transmitted, it is a practical way to stimulate muscles for rehabilitation or training purposes. However, myoelectric signals, which are emitted by the muscles, are often picked up via the electrodes and fed to a prosthesis control system, for example. This renders it possible to control prosthesis elements, such as a prosthetic hand.

Regardless of the direction in which the electrical signals are to be transmitted, an electrical connection between the electrode of the liner and an electronic data processing device must be established, wherein said data processing device may be arranged in or on the prosthesis socket, for example. In the specified publications U.S. Pat. No. 9,744,056 B2 and U.S. Pat. No. 9,155,634, this electrical contact occurs at the distal end, as there is an area of contact between the liner and the prosthesis socket here anyway. DE 10 2014 106 070 A1 describes a liner which allows for an electrical contacting on the lateral surface. However, to this end the liner must be arranged in the exactly the required position on the amputation stump in order to ensure contacting occurs in the correct way.

A socket system is known from WO 2008/040286 A1 that consists of an outer socket and an inner socket. In this case, the outer socket has several elements which can be slightly moved, for example bent up, relative to one another. To achieve an optimum form-fit, the inner socket is equipped on its lateral surface with a mechanical locking element, which can interact with a counter-element of the prosthesis socket, thereby enabling the two socket elements to connect.

The problem with using liners is that they often have a rotationally symmetrical cross-section and can therefore be arranged in a number of different positions on the amputation stump. However, in order to be able to pick up myoelectric signals from the desired point or to apply them to the desired muscles, it is necessary that the liner is arranged precisely on the amputation stump so the electrodes are in the desired and required position on the amputation stump.

SUMMARY

The invention therefore aims to further develop a prosthesis system so that these demands can be met as easily as possible.

The invention solves the problem by way of a prosthesis system according to the present disclosure, wherein the first connection device is arranged on the lateral surface, and the first connection device and the second connection device are configured to establish a mechanical locking and an electrical contact between the liner and the prosthesis socket.

Unlike with devices of the prior art, the first connection device is arranged on the lateral surface, i.e. between the distal end and the proximal end. This refers in particular to the area in which the liner has an annular cross-section. There is often a liner cap or liner cup at the distal end, wherein said cap or cup has only a circular, solid cross-section when cut perpendicular to the longitudinal extension of the liner. The longitudinal extension or longitudinal direction of a liner extends from the distal end to the proximal end. The positioning of the first connection device on this lateral surface creates a range of advantages. First, the wearer of the prosthesis system is able to clearly recognise when mounting the liner whether the liner can be arranged in the right orientation on the amputation stump. The first connection device arranged on the outer side of the liner, said connection device protruding radially outwards, provides the wearer with a good indicator for this crucial correct alignment of the liner.

In order to ensure that the second connection device, which is arranged on the prosthesis socket, can interact with the thus arranged first connection device, it must be arranged at the same height of the prosthesis socket, i.e. also not in the distal region. This is particularly beneficial if the wearer of the prosthesis system has a long amputation stump. In this case, it is possible that there is not enough installation space distal to the liner to arrange the corresponding connection devices. This problem is also solved by the configuration according to the invention.

Given that the electrical contact between liner and prosthesis socket is also established by way of the first connection device of the liner and the second connection device of the prosthesis socket, it is necessary to conduct the electrical signals into the distal region of the amputation stump and the liner, and from there to transmit them into the prosthesis socket. They would then have be conducted to another electronic data processing device, possibly not arranged in the distal region. The prosthesis liner may be equipped with electrodes and/or sensors for detecting bio-signals. Bio-signals are generally myoelectric signals, for example, and/or impedance signals, especially bio-impedance signals. Additionally or alternatively, the liner may also have at least one, preferably several, stimulation electrodes, so that signals can be sent to the amputation stump and the skin of the wearer of the liner.

The first and second connection devices preferably comprise positive-locking elements that correspond with one another. For example, these may be latch elements and corresponding undercut elements. The latch elements, which may form part of either the first or second connection device, are moved upon insertion of the liner into the prosthesis socket relative to the undercut elements, which form part of the respective other connection device, in such a way that they latch behind the undercut elements, thereby effecting a locking. Of course, other positive-locking elements are also possible.

Preferably, the liner and the prosthesis socket are locked against both rotational and translational movement by the mechanical locking of the two connecting devices. On the one hand, this prevents the prosthesis socket from moving relative to the liner in a rotational movement about the amputation stump; on the other hand, it means that the liner cannot be removed from the prosthesis socket, for instance if the prosthesis socket is subjected to tension.

The liner preferably comprises at least one electrode, which is connected to the first connection device via at least one electric conductor. It is especially preferable if the liner has several electrodes, for example two, three or four, each of which comprises an electric conductor that is connected to the connection device. In this case in particular, it is practical to establish several electrical contacts in order to control each electrode individually and to be able to individually process the signals picked up by the electrodes.

In a preferred configuration, the prosthesis socket has or can be connected to an electronic data processing device which can be connected to the at least one electrode via the electrical contact. Alternatively or additionally, the liner features an electronic data processing device and the electrical contact only serves to establish a power supply. In this case, the prosthesis socket has an appropriate source of energy, such as a rechargeable battery or a battery, by way of which the power supply of the electronic data processing device can be ensured, wherein said data processing device may form part of the liner or the prosthesis socket.

Preferably, a first diameter of the liner at the distal end is greater in a first direction than a second diameter in a second direction, which extends orthogonally to this first direction. It is especially preferable if the first diameter is the maximum diameter. It has been proven particularly beneficial if, in this case, the second diameter is the minimum diameter. Such liners are especially—but not exclusively—practical for lower arm amputees. While a liner for an upper leg amputee may have a circular cross-section, as the cross-section of an upper leg is almost circular as well, this is not the case with lower arms. Furthermore, the contouring of the liner in this form already ensures that it cannot be twisted and provides a mounting support. The cross-section of the liner may be designed to be oval, irregular or quadrangular, wherein the corners of a quadrangular configuration should be rounded.

Preferably, the first connection device is arranged on the outer side as an extension of the second diameter.

It has been proven beneficial if a ratio of the first diameter to the second diameter varies between the distal end and the proximal end. This means that at different points along the longitudinal extension of the liner, i.e. from the distal end to the proximal end, there are different ratios of the corresponding diameters. This renders it especially easy to take into account any individual circumstances.

The invention also solves the problem by way of a liner for a corresponding prosthesis system and a prosthesis socket for such a prosthesis system.

BRIEF DESCRIPTION OF THE DRAWINGS

In the following, examples of embodiments of the present invention will be explained in more detail by way of the attached figures: They show.

DETAILED DESCRIPTION

Figure 1:
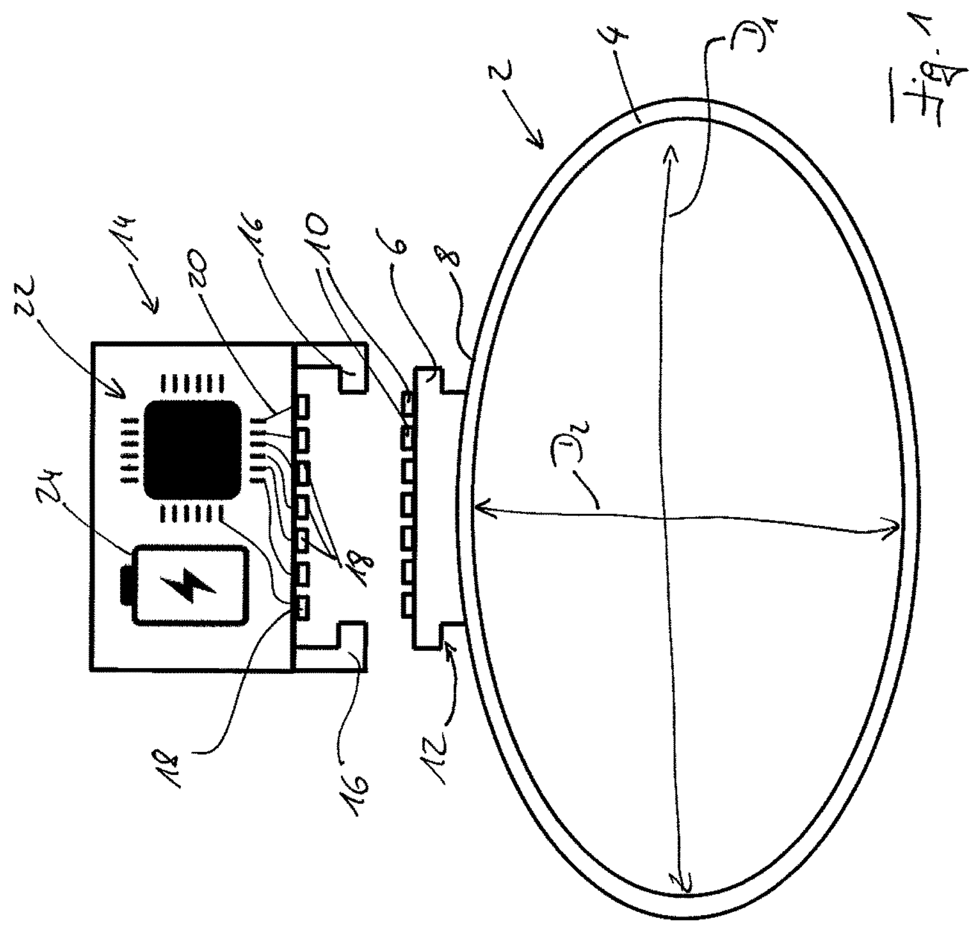
FIG. 1 the schematic depiction through a section of a prosthesis system according to an example of an embodiment of the present invention, FIG. 2 the schematic sectional view through a section of a prosthesis system according to another example of an embodiment of the present invention, FIGS. 3*a* and 3*b* two different examples of an embodiment of a liner, FIG. 4 the schematic view and sectional view through a liner for a prosthesis system according to an example of an embodiment of the present invention, and FIGS. 5 and 6 sectional views through prosthesis systems according to examples of an embodiment of the present invention.

FIG. 1 shows a liner 2 in a sectional view. The lateral surface 4 is shown in a sectional view. The liner does not have a circular cross-section, but rather a first diameter $D_1$ and a second diameter $D_2$ perpendicular to it, wherein said second diameter is smaller than the first diameter $D_1$. As an extension of the second diameter $D_2$, a first connection device 6 is arranged on an outer side 8 of the liner 2. It has electrical contacts 10 and two projections 12, by way of which the electrical contact and the mechanical locking can be achieved.

A second connection device 14 forms part of a prosthesis socket, not depicted, which comprises two hook elements 16 that interact with the projections 12 of the first connection device 6. When the hooks 16 engage with the projections 12, electrical contacts 18 of the second connection device rest on the electrical contacts 10 of the first connection device 8 and the electrical connection is established. Electric conductors 20 serve to connect the electrical contacts 18 to an electronic data processing device 22, which is depicted schematically. An energy source 24 supplies said device with electrical energy.

Figure 2:
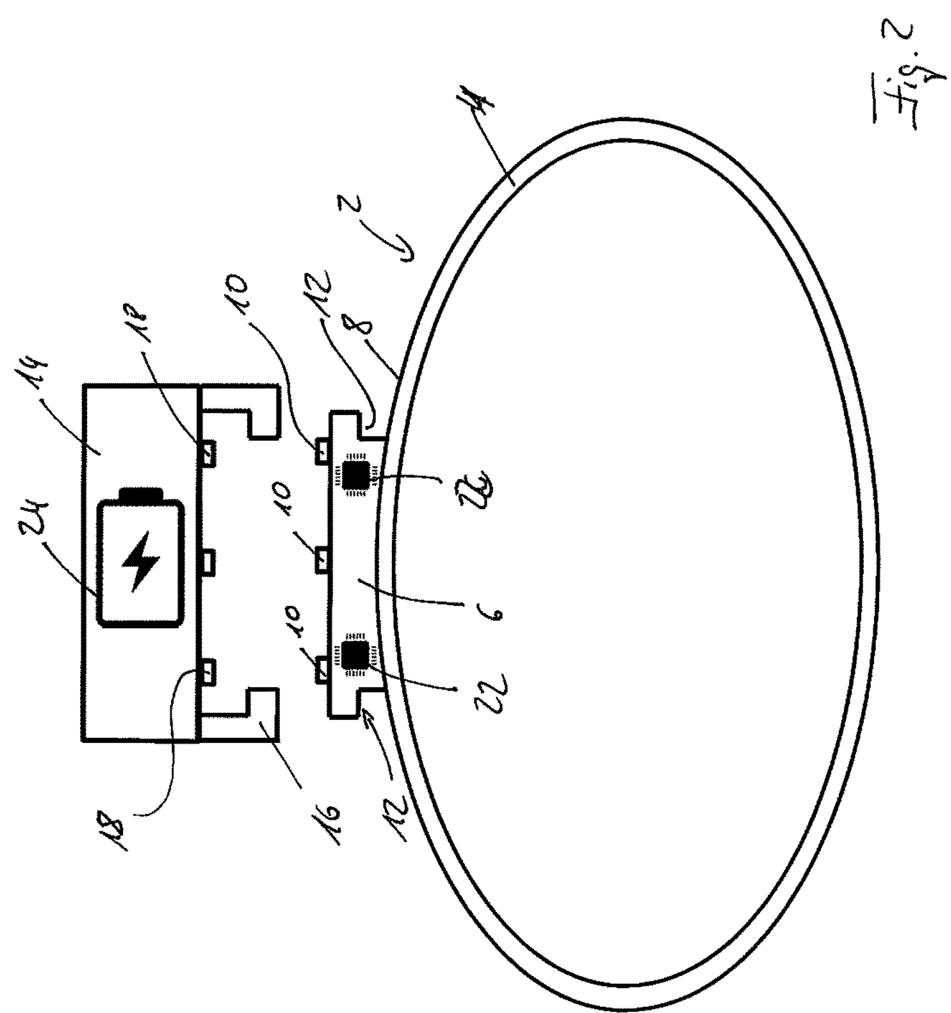

FIG. 2 shows an alternative configuration. Again, the lateral surface 4 of the liner 2 does not have a circular cross-section. Electrical contacts 10 are again arranged on the first connection device 6, which is also arranged on the outer side 8 of the liner 2; however, there are now considerably fewer of said electrical contacts. They can be brought into contact with the electrical contacts 18 on the second connection device 14 if the hook elements 16 with the projections 12 are engaged with the first connection element 6. The second connection device 14 comprises an energy source 24, by way of which the electronic data processing device 22, which forms part of the first connection device 6 in the example of an embodiment shown, is supplied with energy.

Figure 3A:
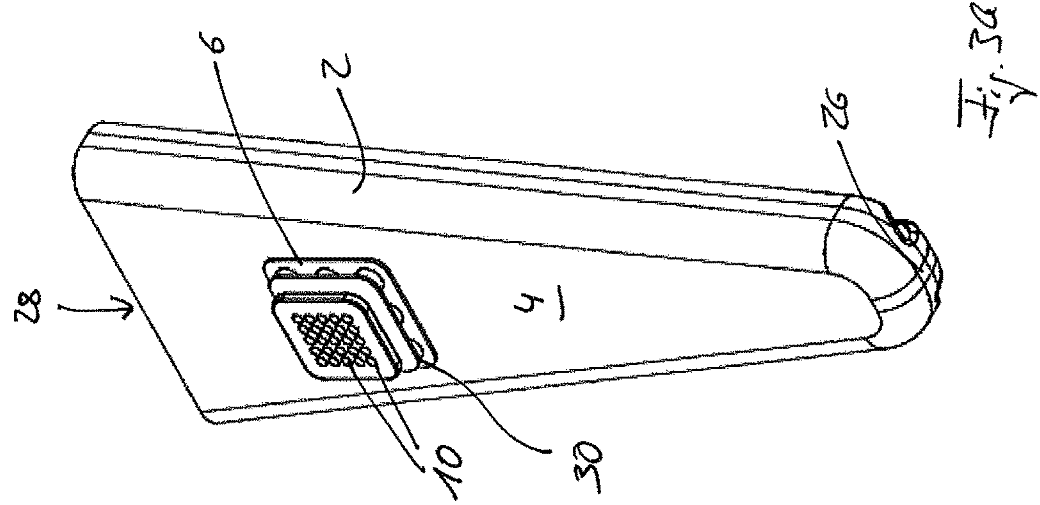
Figure 3A:
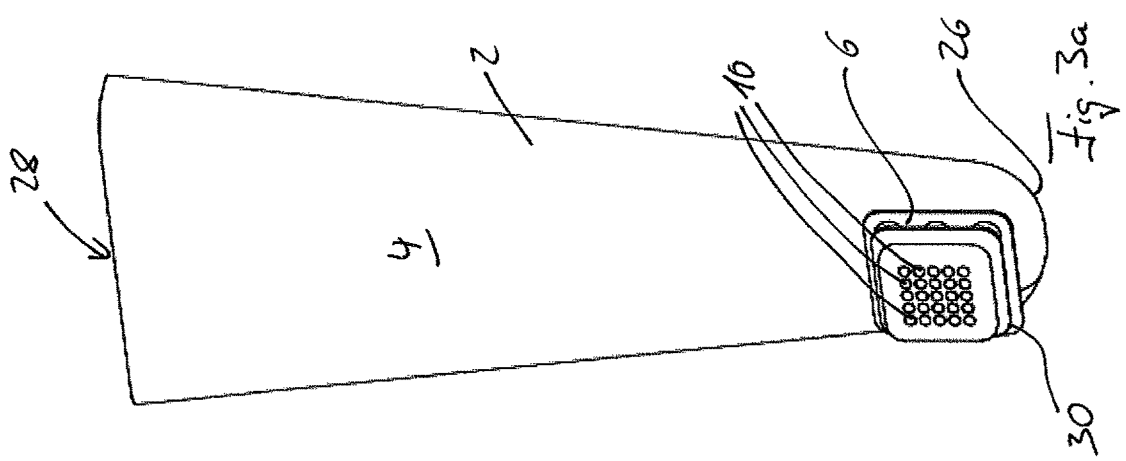

FIGS. 3*a* and 3*b* depict two liners 2 for a prosthesis system of the type described here. They feature a closed distal end 26 and an open proximal end 28. The lateral surface 4 extends between them. The first connection device 6 is arranged on the lateral surface 4, said connection device having several electrical contacts 10 arranged in a square pattern. The connection to a second connection device 14, not depicted, can be established via undercut elements 30.

The left-hand representation in FIG. 4 depicts a liner 2 for an example of an embodiment of the present invention. It features several electrodes 32, each of which is connected to the electrical contacts 10 of the first connection device 6 via an electric conductor 34. The electric conductors 34 extend inside the material of the liner 2. The right-hand representation in FIG. 4 depicts the sectional view along the line C-C. The liner 2 with the electric conductors 34 inside the liner material can be clearly seen, wherein said electric conductors lead to the electrodes 32 and are connected to the first connection device 6.

FIG. 5 shows a schematic view on the left and a sectional view on the right through a prosthesis system according to an example of an embodiment of the present invention. The liner 2 is positioned over an amputation stump, not depicted, similar to the one depicted in FIG. 4. The liner 2 features electrodes 32 which are connected to the electrical contacts 10 of the first connection device 6 via electric conductors 34. A prosthesis socket 36 is positioned over said liner, wherein a prosthetic hand 38 is situated on said socket. The prosthesis socket 36 is shown to be transparent in order to render visible the electronic data processing device 22 and the energy source 24, which are arranged inside the prosthesis socket 26 and connected to the second connection device 14. The prosthesis socket 36 is conventionally not designed to be transparent.

The right-hand representation in FIG. 5 shows a cut along the line A-A. The liner 2, the base body of the prosthesis socket 36 as well as the first connection device 6 and the second connection device 14 can be seen. The hook elements 16 of the second connection device 14 engage behind the projections 12 of the first connection device 6, thereby ensuring a mechanical locking. At the same time, the electrical contacts 10 of the first connection device 6 come into contact with the electrical contacts 18 of the second connection device 14.

FIG. 6 depicts a prosthesis system according to another example of an embodiment of the present invention. To the left of FIG. 6, a schematic view is presented in which a prosthesis socket 36 is depicted, which is situated in a liner 2 not depicted here. Only the electrodes 32 and the electric conductors 34 of the liner are shown, the latter serving to connect the electrodes 32 with the electrical contact 10 of the first connection device 6. The liner itself is not shown for reasons of clarity. A prosthetic foot 40 is arranged the distal, i.e. lower, end of the prosthesis socket 36. The energy source 24 and the electronic data processing device 22 are situated on a lower leg element arranged between the prosthetic foot 40 and the prosthesis socket 36. The right-hand representation in FIG. 6 shows a cut along the line B-B with the liner 2, the prosthesis socket 36 as well as the first connection device 6 and the second connection device 14. Here too, there is both a mechanical locking between the two connecting devices 6, 14 as well as contact between the respective electrical contacts 10, 18.

The prosthesis device, especially in the embodiments shown in FIGS. 5 and 6, may have further sensors in order to detect, for example, operational requirements. The prosthesis device preferably has kinetic sensors, such as force or torque sensors, and/or kinematic sensors, such as acceleration, speed or position sensors, and/or environmental sensors, such as optical sensors, ultrasound, a radar or receptors for RFID tags.

We claim:

1. A prosthesis system comprising:
- a liner comprising:
  - a closed distal end;
  - an open proximal end;
  - a lateral surface, which extends from the distal end to the proximal end; and
  - a first connection device; and
- a prosthesis socket comprising:
  - a second connection device, which is configured to interact with the first connection device;
  - wherein the first connection device is arranged on the lateral surface, and the first connection device and the second connection device are configured to establish a mechanical locking and an electrical contact between the liner and the prosthesis socket.

2. The prosthesis system according to claim 1, wherein the first connection device and the second connection device comprise mechanical locking elements that correspond with one another.

3. The prosthesis system according to claim 1, wherein the liner and the prosthesis socket are locked against a rotational movement and a translational movement by the mechanical locking.

4. The prosthesis system according to claim 1, wherein the liner comprises at least one of at least one electrode, at least one sensor, and at least one stimulation device, which is connected to the first connection device via at least one electric conductor.

5. The prosthesis system according to claim 4, wherein the prosthesis socket comprises or can be connected to an electronic data processing device, which can be connected via the electrical contact to the at least one electrode.

6. The prosthesis system according to claim 1, wherein a first diameter of the liner at the distal end is greater in a first direction than a second diameter of the liner in a second direction, which extends orthogonally to the first direction.

7. The prosthesis system according to claim 6, wherein the first connection device is arranged on the an outer side as an extension of the second diameter.

8. The prosthesis system according to claim 6, wherein a ratio of the first diameter to the second diameter varies between the distal end and the proximal end.

9. A prosthesis socket for a prosthesis system, wherein the prosthesis system includes a liner including: a closed distal end; an open proximal end: a lateral surface, which extends from the distal end to the proximal end; and a first connection device arranged on the lateral surface of the liner, the prosthesis socket comprising:
- a closed distal end;
- an open proximal end;
- a lateral surface, which extends from the distal end to the proximal end; and
- a second connection device which is configured to interact with the first connection device on the lateral surface of the liner;

wherein the first connection device and the second connection device are configured to establish a mechanical locking and an electrical contact between the liner and the prosthesis socket.

10. A prosthesis system comprising:

a liner comprising:

a closed distal end;

an open proximal end;

a lateral surface extending from the distal end to the proximal end; and a first connection device arranged on the lateral surface; and a prosthesis socket comprising a second connection device that interacts with the first connection device to establish a mechanical locking and an electrical contact between the liner and the prosthesis socket.

11. The prosthesis system according to claim 10, wherein the first connection device and the second connection device comprise mechanical locking elements that correspond with one another.

12. The prosthesis system according to claim 10, wherein the liner and the prosthesis socket are lockable against a rotational movement and a translational movement by the mechanical locking.

13. The prosthesis system according to claim 10, wherein the liner comprises at least one of at least one electrode, at least one sensor, and at least one stimulation device, which is connected to the first connection device via at least one electric conductor.

14. The prosthesis system according to claim 13, further comprising an electronic data processing device connected via the electrical contact to the at least one electrode, and the prosthesis socket comprises or can be connected to the electronic data processing device.

15. The prosthesis system according to claim 10, wherein a first diameter of the liner at the distal end is greater in a first direction than a second diameter of the liner in a second direction, the second direction oriented orthogonally relative to the first direction.

16. The prosthesis system according to claim 15, wherein the first connection device is arranged on the outer side as an extension of the second diameter.

17. The prosthesis system according to claim 15, wherein a ratio of the first diameter to the second diameter varies between the distal end and the proximal end.

* * * * *